United States Patent [19]

Zaiger et al.

[11] Patent Number: Plant 7,305

[45] Date of Patent: Aug. 21, 1990

[54] NECTARINE TREE "APRIL GLO"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 388,891

[22] Filed: Aug. 2, 1989

[51] Int. Cl.[5] ..... A01H 5/00

[52] U.S. Cl. ..... Plt./40

[58] Field of Search ..... Plt./40

*Primary Examiner*—James R. Feyrer

[57] ABSTRACT

A new and distinct variety of nectarine tree having the following unique combination of outstanding features that are desirable in a new variety:

1. Early maturity of the fruit, May 15, 1989.
2. Low winter chilling requirement, approximately 200 hours.
3. Fruit with good flavor and eating quality.
4. Fruit with good shipping quality.
5. Heavy and regular production of fruit.
6. Relatively uniform fruit size throughout the tree.
7. Vigorous, upright tree growth.

1 Drawing Sheet

ORIGIN OF THE VARIETY

The new nectarine tree was originated by us in the experimental orchard located at Modesto, Calif. as a first generation cross between selected seedlings with the identification numbers 4E467LC and 26G520. The selected female parent 4E467LC originated from a cross between Ruby Gold Nectarine (U.S. Pat. No. P.P. 3,101) an a peach of unknown parentage with a low winter chilling requirement. The selected pollen parent 26G520 originated from a cross between Sun Red Nectarine (Non-patented) and Royal Peach (U.S. Pat. No. P.P. 3,411). A large group of seedlings from this first generation cross were grown and maintained under close observation, one such early maturing seedling with a low chilling requirement exhibiting desirable fruit characteristics was selected for asexual reproduction and commercialization.

ASEXUAL REPRODUCTION OF THE VARIETY

Asexual reproduction of the new variety of nectarine tree was preformed in the experimental orchard located at Modesto, Calif. by budding and shows that said characteristics run true to form and are established and transmitted through succeeding propagations.

SUMMARY OF THE VARIETY

The herein new variety of nectarine tree is of large size, vigorous, upright growth, has a low winter chilling requirement of approximately 200 hours and being a regular and productive bearer of early maturiting nectarines in warm winter areas such as Palm Desert, Calif. The present variety is further characterized by producing medium size, yellow flesh, semi freestone fruit with good flavor and eating quality and having an attractive red skin color. The fruit maturing approximately 10–14 days earlier than the low chilling nectarine variety May Gold (U.S. Pat. No. P.P. 5,245).

PHOTOGRAPHS OF THE VARIETY

The accompanying photographs show typical specimens of the foliage and fruit of the new variety. The upper and lower surface of the leaves being illustrated and the exterior and sectional view of the fruit with a fruit divided in its suture plane to reveal flesh coloration with a stone remaining in place. The illustrations were taken shortly after being picked at maturity (shipping ripe) and the colors are as nearly true as reasonable possible in a color representation of this type.

DESCRIPTION OF THE VARIETY

A detailed botanical description of the new variety of nectarine tree, its fruit, flowers and foliage, based on observations of specimens grown at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Production.*—Productive.
- *Density.*—Medium dense.
- *Bearing.*—Regular.

Trunk:
- *Size.*—Medium to large.
- *Texture.*—Shaggy.
- *Color.*—Brown to dull brown—(5-E-3) to (6-F-4).

Branches:
- *Size.*—Medium.
- *Texture.*—Medium rough.
- *Lenticels.*—Numerous. Medium size.

Leaves:
- *Size.*—Large. Average length—6". Average width—$1\frac{3}{8}$"–$1\frac{1}{2}$".
- *Form.*—Lanceolate.
- *Margin.*—Crenate.
- *Petiole.*—Medium length. Medium thickness.
- *Glands.*—Globose. Number varies 0 to 3. Average number 2. Located primarily on base of leaf blade.
- *Color.*—Green to deep green—upper surface (27-E-7) to (27-F-7). Grayish green—lower surface (27-D-6) to (27-E-6).

Flower buds:
- *Size.*—Medium size. Medium length.
- *Form.*—Plump.

Flowers:

*Size.*—Medium—non showy.

*Blooming period.*—Feb. 6 to Feb. 16, 1989. Varies slightly with climatic conditions.

*Pollen.*—Present.

*Color.*—Pink.

Fruit:

*Maturity when described.*—Shipping ripe.

*Date of first picking.*—May 15, 1989.

*Date of last picking.*—May 21, 1989.

*Size.*—Medium. Average diameter axially—2⅜" to 2½". Average transversely to suture plane—2⅜" to 2½".

*Form.*—Globose.

*Suture.*—Pronounded, extends from apex to base.

*Ventral surface.*—Slightly lipped.

*Cavity.*—Rounded, slightly elongated in sutur plane. Average depth—⅜". Average breadth—½".

*Apex.*—Rounded to slight depression.

*Base.*—Usually rounded, some fruit slightly extended on one side.

Skin:

*Thickness.*—Medium.

*Texture.*—Tough, tenacious to flesh.

*Tendency to crack.*—None.

*Color.*—Yellow to yellow orange ground color—(4-A-8) to (5-A-8). Overspread with red to dark red—(10-A-8) to (10-D-8).

*Down.*—Wanting.

Flesh:

*Texture.*—Firm.

*Ripens.*—Even.

*Juice.*—Moderate.

*Flavor.*—Good—sub-acid.

*Eating quality.*—Good.

*Fibers.*—Small and tender.

*Color.*—Light yellow to yellow—(4-A-6) to (4-A-8).

Stone:

*Type.*—Semi-freestone. Flesh adheres to stone in very limited areas.

*Size.*—Large. Average length—1⅜". Average width—1 1/16". Average thickness—¾".

*Base.*—Varies from straight to rounded.

*Apex.*—Rounded to slightly pointed.

*Surface.*—Irregularly furrowed toward apex, pitted toward base.

*Tendency to split.*—Very slight.

*Color.*—Light brown—(7-B-6) to (7-C-6).

Use: Dessert.

Keeping quality: Good.

Shipping quality: Good.

The nectarine tree, its foilage, flowers and fruit herein described may vary in slight detail due to climatic, soil and ecological conditions under which the variety may be grown; the present botanical description is that of the variety produced and grown under the conditions prevailing at Modesto, Calif.

The following is claimed:

1. A new and distinct variety of nectarine tree substantially as illustrated and described, characterized by its low chilling requirement of approximately 200 hours, its large size, vigorous, upright growth and being a regular and productive bearer of medium size, early maturing, yellow flesh, semi freestone fruit with good flavor and eating quality; the fruit is further characterized by having good shipping quality and maturing approximately 10–14 days before the low chilling nectarine variety May Glo, U.S. Pat. No. P.P. 5,245.

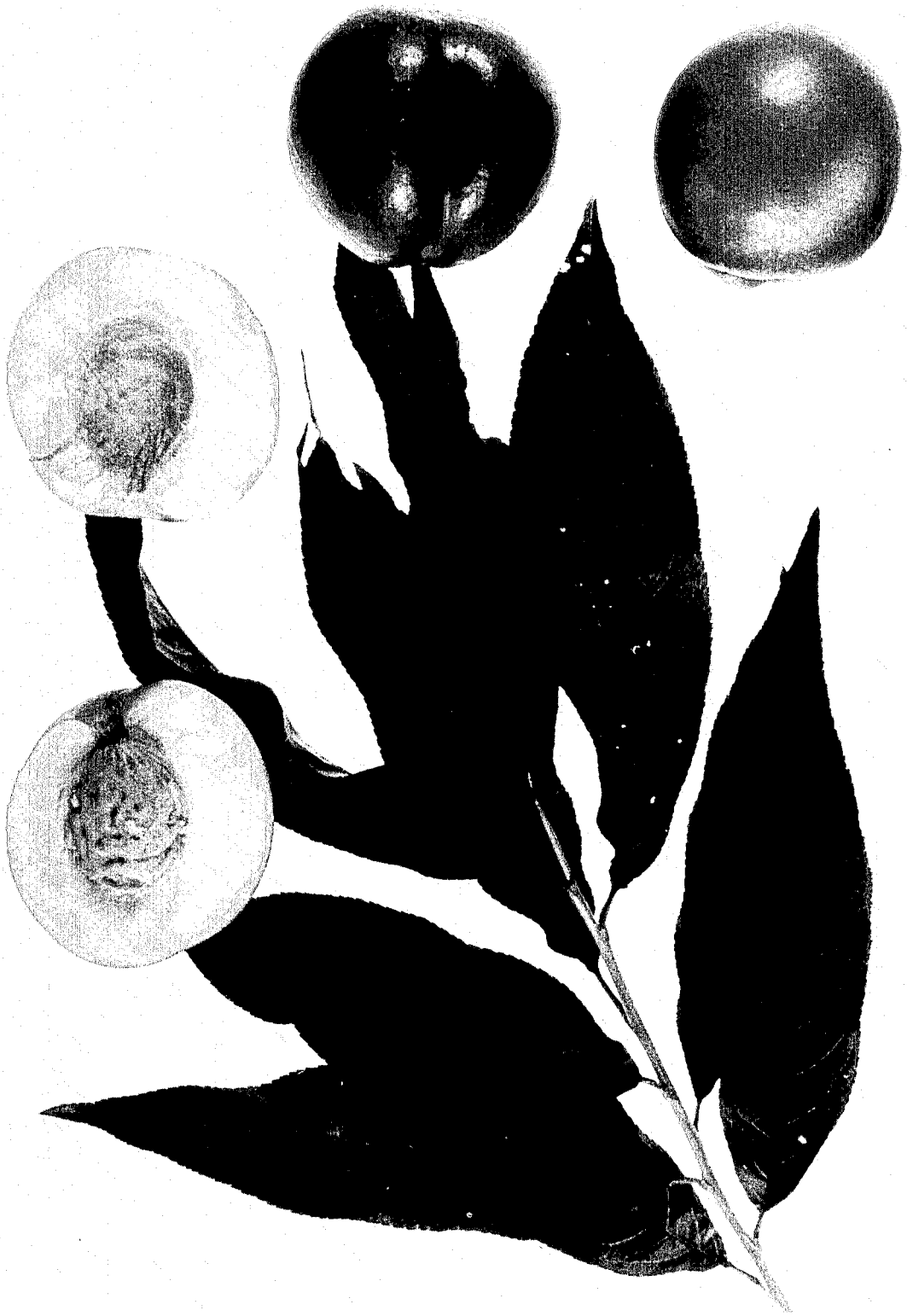

* * * * *